United States Patent [19]

Sano et al.

[11] Patent Number: 5,254,688

[45] Date of Patent: Oct. 19, 1993

[54] PROCESS FOR PRODUCING PYRIDO[1,2-A]PYRIMIDINE DERIVATIVE

[75] Inventors: Atsunori Sano; Motoshige Sumino, both of Saitama; Masami Ishihara, Fukaya; Kazuo Maruhashi, Kawagoe, all of Japan

[73] Assignee: Wako Pure Chemical Industries, Ltd., Osaka, Japan

[21] Appl. No.: 717,591

[22] Filed: Jun. 19, 1991

[30] Foreign Application Priority Data

Jun. 21, 1990 [JP] Japan ................................. 2-163618

[51] Int. Cl.$^5$ ............................. C07D 239/10; 544 282
[52] U.S. Cl. ..................................... 544/282; 546/276
[58] Field of Search ......................................... 544/282

[56] References Cited

U.S. PATENT DOCUMENTS 4,474,953 10/1984 Wade .................................. 544/282
5,081,243 1/1992 Sano et al. ......................... 544/282

FOREIGN PATENT DOCUMENTS 0385634 9/1990 European Pat. Off. .

OTHER PUBLICATIONS

Patent Abstracts of Japan, vol. 13, No. 56 (C-566)[3404], Feb. 8, 1989; & JP-A-63 246 374.

Primary Examiner—Thurman K. Page
Assistant Examiner—Jyothsna Venkat
Attorney, Agent, or Firm—Armstrong, Westerman, Hattori, McLeland & Naughton

[57] ABSTRACT

A pyrido[1,2-a]pyrimidine derivative which is useful as an antiallergic agent can be produced from a 2-aminopyridine derivative or a hydrazoic acid salt thereof by a one-pot and substantially one-step process.

2 Claims, No Drawings

PROCESS FOR PRODUCING PYRIDO[1,2-A]PYRIMIDINE DERIVATIVE

BACKGROUND OF THE INVENTION

This invention relates to a process for producing a pyrido[1,2-a]pyrimidine derivative which is useful as an antiallergic agent.

Pyrido[1,2-a]pyrimidine derivatives and salts thereof are known as drugs having antiallergic activity. Various antiallergic agents containing such compounds as an effective component are widely used. Processes for producing such compounds are disclosed, for example, in Japanese Patent Unexamined Publication Nos. 63-183581, 63-246374, 63-246375, etc. According to these processes, pyrimidine derivatives or pyridine derivatives containing a cyano group are synthesized from commercially available compounds, followed by reaction with hydrazoic acid or a salt thereof to form a tetrazole ring, thus giving the desired compounds by multistep synthesis. Further, U.S. Pat, No. 4,474,953 discloses a process for producing a pyrido[1,2-a]pyrimidine derivative by reacting a 2-aminopyridine derivative, a tetrazol-5-yl acetic acid ester and an orthoformic acid ester in the presence of a Lewis acid to yield a 3-[N-(2-pyridyl)-amino]-2-(1 H-tetrazol-5-yl)acrylate derivative, which is then separated and heated at 100° to 150° C. in polyphosphoric acid for ring closure. This process employs a two-step reaction using different catalysts in both steps with complicated procedures.

Since pyrido[1,2-a]pyrimidine derivatives have a very complicated structure, these compounds have been usually synthesized by multi-step reactions, resulting in increasing in production time, man power, production apparatus, and production cost.

SUMMARY OF THE INVENTION

It is an object of the present invention to provide a process for producing a pyrido[1,2-a]pyrimidine derivative in one-pot and substantially one-step reaction using commercially available starting materials.

The present invention provides a process for producing a compound of the formula:

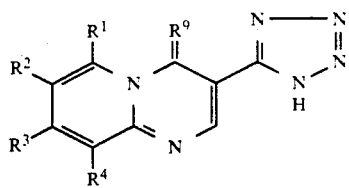

(I)

wherein $R^1$ and $R^3$ are independently a hydrogen atom or a lower alkyl group; $R^2$ and $R^4$ are independently a hydrogen atom, a halogen atom, a lower alkyl group, a lower alkoxy group, a phenyl group or a group of the formula:

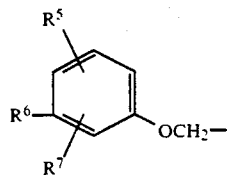

(II)

wherein $R^5$ is a hydrogen atom or a hydroxyl group; $R^6$ is a hydrogen atom or an acyl group; and $R^7$ is a hydrogen atom, a lower alkyl group or an allyl group; and $R^9$ is an oxygen atom or an imino group, in one-pot and in substantially one-step process using a compound of the formula:

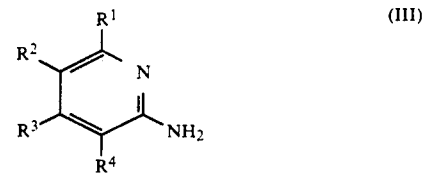

(III)

wherein $R^1$ to $R^4$ are as defined above, or a hydrazoic acid salt of the compound of the formula (III), as a starting material, to yield a compound of the formula:

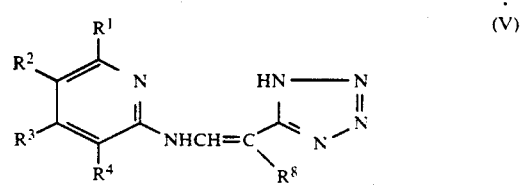

(V)

wherein $R^1$ to $R^4$ are as defined above; and $R^8$ is a lower alkoxycarbonyl group or a cyano group. followed by ring closure reaction to give the desired compound of the formula (I) without separation from the reaction solution.

DESCRIPTION OF THE PREFERRED EMBODIMENTS

According to the process of the present invention, a pyrido[1,2-a]pyrimidine derivative of the formula:

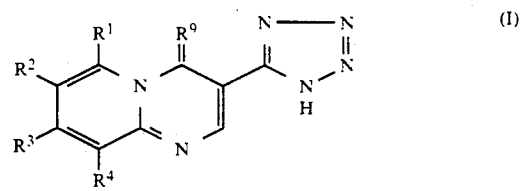

(I)

wherein $R^1$ and $R^3$ are independently a hydrogen atom or a lower alkyl group preferably having 1 to 6 carbon atoms; $R^2$ and $R^4$ are independently a hydrogen atom, a halogen atom, a lower alkyl group preferably having 1 to 6 carbon atoms, a lower alkoxy group preferably having 1 to 6 carbon atoms, a phenyl group or a group of the formula:

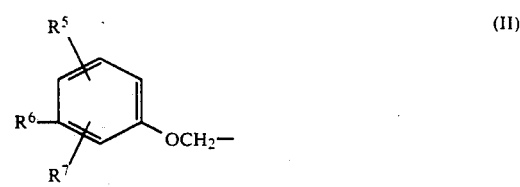

(II)

wherein $R^5$ is a hydrogen atom or a hydroxyl group; $R^6$ is a hydrogen atom or an acyl group; and $R^7$ is a hydrogen atom, a lower alkyl group preferably having 1 to 6 carbon atoms or an allyl group; $R^9$ is an oxygen atom or an imino group, can be produced in one-pot and in substantially one-step process using a compound of the formula:

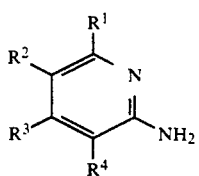
(III)

wherein R¹ to R⁴ are as defined above, or a hydrazoic acid salt of the compound of the formula (III), as a starting material, to yield a compound of the formula:

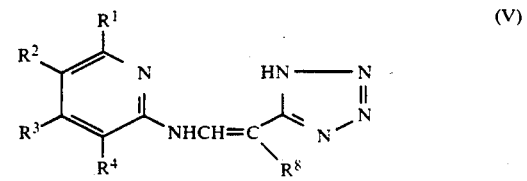
(V)

wherein R¹ to R⁴ are as defined above; and R⁸ is a lower alkoxycarbonyl group or a cyano group, followed by ring closure reaction to give the desired compound of the formula (I) without separation from the reaction solution.

More concretely, the compound of the formula (I) can be produced by the following three processes (A) to (C).

Process (A):

The compound of the formula (I) can be produced by reacting a compound of the formula (III), a compound of the formula:

(IV)

wherein R⁸ is a lower alkoxycarbonyl group preferably having 2 to 7 carbon atoms, or a cyano group, and an alkyl orthoformate in the absence of a catalyst to yield a compound of the formula (V), followed by ring closure reaction without separation from the reaction solution.

Process (B):

The compound of the formula (I) can also be produced by reacting a hydrazoic acid salt of the compound of the formula (III) with a compound of the formula:

(VI)

wherein R⁸ is as defined above; and R¹⁰ is a hydrogen atom or a lower alkyl group preferably having 1 to 6 carbon atoms, in the absence of a catalyst to yield the compound of the formula (V), followed by ring closure reaction without separation from the reaction solution.

Process (C):

The compound of the formula (I) can further be produced by reacting a hydrazoic acid salt of the compound of the formula (III) with a compound of the formula:

$$R^8CH_2CN \quad (VII)$$

wherein R⁸ is as defined above, and an alkyl orthoformate in the absence of a catalyst to yield the compound of the formula (V), followed by ring closure reaction without separation from the reaction solution.

The term "lower alkyl group" in the definition of R¹ to R⁴, R⁷ and R¹⁰ includes straight-chain or branched-chain alkyl groups having preferably 1 to 6 carbon atoms such as a methyl group, an ethyl group, a propyl group, a butyl group, an amyl group, etc.

The term "halogen atom" in the definition of R² and R⁴ includes a chlorine atom, a bromine atom, a fluorine atom and an iodine atom.

The term "lower alkoxy group" in the definition of R² and R⁴ includes straight-chain or branched-chain alkoxy groups having preferably 1 to 6 carbon atoms such as a methoxy group, an ethoxy group, a propoxy group, a butoxy group, an amyloxy group, etc.

The term "acyl group" in the definition of R⁶ includes an acetyl group, a propionyl group, a butylyl group, a benzoyl group, etc.

The term "lower alkoxycarbonyl group" in the definition of R⁸ includes straight-chain or branched-chain alkoxycarbonyl group preferably having 2 to 7 carbon atoms such as a methoxycarbonyl group, an ethoxycarbonyl group, a propoxycarbonyl group, a butoxycarbonyl group, an amyloxycarbonyl group, etc.

The term "alkyl" in the alkyl orthoformate includes lower straight-chain or branched-chain alkyl group preferably having 1 to 6 carbon atoms such as a methyl group, an ethyl group, a propyl group, a butyl group, an amyl group, etc.

In the processes of the present invention, the compound of the formula (III) used as a starting material is available commercially, and can be used as it is or after purified, if necessary. The compound of the formula (III) can be synthesized by a process disclosed, for example, in Org. React., vol. 1, pp 91–104 (1942). The compounds of the formulae (IV), (VI), (VII), and alkyl orthoformate can also be available commercially.

The hydrazoic acid salt of the compound of the formula (III) can easily be produced by salt exchange of an acid adduct of the compound of the formula (III) with a hydrazoic acid salt such as sodium azide. Further, the hydrazoic acid salt of the compound (III) can also be produced by adding an acid such as hydrochloric acid, sulfuric acid, or the like to a mixture of the compound of the formula (III) and a hydrazoic acid salt such as sodium azide. These reactions can be carried out in the same reactor for synthesizing the compound of the formula (V).

The processes of the present invention are explained in detail below.

(1) Process (A):

A compound of the formula (III) and a compound of the formula (IV) are mixed at a predetermined temperature such as 70°–90° C. in the presence of an alkyl orthoformate to yield a compound of the formula (V), which is subjected to ring closure reaction as it is in the presence of an acid or base, or simply with heating, to yield a compound of the formula (I). The producing reaction of the compound of the formula (V) is usually carried out in an organic solvent. When the alkyl orthoformate is liquid, the reaction can be carried out in the absence of solvent.

As the organic solvent, there can be used those which do not inhibit the reaction and do not react by themselves such as alcohols, e.g. methanol, ethanol, isopropanol, etc.; ketones, e.g. acetone, methyl ethyl ketone, etc.; esters, e.g. methyl acetate, ethyl acetate, etc.; aromatic hydrocarbons, e.g. benzene, toluene, xylene, etc.; halogenated hydrocarbons, e.g. methylene chloride, chloroform, carbon tetrachloride, dichloroethane, etc.; nitriles, e.g. acetonitrile, propionitrile, etc.; ethers, e.g. diethyl ether, tetrahydrofuran, dioxane, ethylene glycol dimethyl ether, etc.; amides, e.g. N,N-dimethylformaide, N,N-dimethylacetamide, etc.; sulfoxides, e.g. dimethyl sulfoxide, etc. These solvents can be used alone or as a mixture thereof. Among these solvents, the use of the alcohols, nitriles, amides, and sulfoxides is preferable.

The amount of the organic solvent is not limited so long as the organic solvent can dissolve the starting materials and not to lower the reaction rate extremely.

The compound of the formula (III) and the compound of the formula (IV) are preferably used in equimolar amounts and the alkyl orthoformate is preferably used in excess with regards to the compound of the formula (III) and the compound of the formula (IV).

The reaction can be carried out at any temperature from 0° C. to the reflux temperature of the reaction solvent or the alkyl orthoformate. Considering shorter reaction time, the reaction with heating is preferable.

The formation of the compound of the formula (V) can be identified by thin layer chromatography (TLC), or the like. After the completion of the formation of the compound of the formula (V), the ring closure reaction can be started without separating the compound of the formula (V) from the reaction solution.

The ring closure reaction can be carried out only with heating without using a catalyst. But the ring closing reaction using an acid or base as a catalyst is preferable for improving the yield and shortening the reaction time.

When $R^8$ is a cyano group, the ring closure reaction is preferably carried out using an acid as a catalyst. On the other hand, when $R^8$ is a lower alkoxycarbonyl group, the ring closure reaction is preferably carried out using a base as a catalyst with a better yield than the above case of using the acid catalyst.

Since the ring closure reaction is usually carried out by adding an acid or a base as a catalyst to the reaction solution for the formation of the compound of the formula (V), the reaction solvent is naturally the same reaction solvent as used for forming the compound of the formula (V). It is possible to add an acidic organic solvent such as acetic acid, formic acid, or the like, hexamethylphosphoramide (HMPA), or water or the like to the reaction solution for forming the compound of the formula (V).

As the acid catalyst for ring closure, there can be used inorganic acids such as hydrochloric acid, sulfuric acid, nitric acid, phosphoric acid, polyphosphoric acid, phosphorus oxychloride, etc.; an organic acid such as acetic acid, formic acid, benzenesulfonic acid, p-toluenesulfonic acid, methanesulfonic acid, etc.; a Lewis acid such as aluminum chloride, zinc chloride, stannic chloride, trifluoroboric acid, hexafluoroantimonic acid, etc.

The amount of the acid catalyst is not limited so long as the acidity of the reaction solution can be maintained in the whole procedure of the ring closure reaction. When an acidic organic solvent such as acetic acid, formic acid, or the like is added to the reaction solution containing the compound of the formula (V), it is not necessary to add an acid catalyst to the reaction solution.

As the base catalyst for ring closure, there can be used a caustic alkali such as sodium hydroxide, potassium hydroxide, etc.; a hydroxide of alkaline earth metal such as magnesium hydroxide, calcium hydroxide, barium hydroxide, etc.; a metal alkoxide such as sodium methoxide, sodium ethoxide, etc.; an organic base such as pyridine, triethylamine, n-propylamine, benzylamine, ethylenediamine, ethanolamine, diethanolamine, triethanolamine, N-methylpyrrolidone, benzyltrimethylammonium hydroxide, 1,8-diazabicyclo[5.4.0]-7-undecene, etc.; and ammonia.

The amount of the base catalyst is sufficient when the reaction solution can be maintained basic during the whole reaction.

When a base catalyst is used, since it is necessary to maintain the reaction solution basic during the whole reaction, it is necessary to add a base in an equivalent weight or more based on the amount of the compound of the formula (V) produced. Thus, in order to obtain a compound of the formula (I), it is necessary to neutralize with an acid.

On the other hand, when the ring closure reaction product is isolated without neutralization, there can be obtained a salt of compound of the formula (I). Thus, when a salt of compound of the formula (I) is necessary as a drug, a salt forming step is not additionally necessary, resulting in advantageously shortening the step.

The ring closure reaction can be carried out at room temperature to the reflux temperature of the reaction solvent. Since higher reaction temperature makes the reaction time shorter, it is preferable to carry out the reaction at 40° C. to the reflux temperature of the reaction solvent used.

After the ring closure reaction, since crystals of the compound of the formula (I) can be deposited when the reaction solution is adjusted to a strongly acidic solution, the crystals are isolated by filtration.

When the resulting compound of the formula (I) is not deposited as crystals even if made strongly acidic depending on solubility of the reaction solvent used, a solvent such as water which does not dissolve the compound of the formula (I) is added to the reaction solution for crystallization by dilution. Alternatively, the reaction solution is concentrated, re-dissolved, extracted, and the like to isolate the ring closure reaction product.

The resulting compound of the formula (I) can be purified in a conventional method depending on purposes.

In the case of isolating physiologically acceptable salts of the compounds of the formula (I), a sufficient amount of basic compound necessary for forming the salt is added at the time of the ring closure reaction, and the resulting reaction product is isolated after the ring closure reaction without neutralization or with a partial neutralization to an extent not to free the compound of the formula (I) so as to obtain the salt of the compound of the formula (I) by a conventional method. This method is particularly effective compared with the case of isolating the compound of the formula (I), followed by salt formation from the viewpoint of simplification of the salt-formation step.

(2) Process (B)

A mixture of a compound of the formula (III) and a hydrazoic acid salt is actioned with an acid, or an acid adduct of a compound of the formula (III) is reacted with a hydrazoic acid salt, to yield a hydrazoic acid salt of compound of the formula (III), which is reacted with a compound of the formula (VI) in the absence of a catalyst to yield the compound of the formula (V), followed by ring closure reaction without separation from the reaction solution in the same manner as described in the Process (A). Thus, in this process, a tetrazole cyclization step is included unlike the Process (A).

As the hydrazoic acid salt, there can be used commercially available azides such as sodium azide, lithium azide, etc.

As the acid, there can be used any acids which are stronger than hydrazoic acid, for example, inorganic acids such as hydrochloric acid, sulfuric acid, etc.; and organic acids such as acetic acid, p-toluenesulfonic acid, etc.

The azide and the acid can be used in amounts of equimolar amounts or more per mole of the compound of the formula (III). But when the azide and the acid are used too much, excess hydrogen azide is generated undesirably from the viewpoint of handling. Thus, the azide and the acid are usually used in amounts of about 1 to 2 moles, respectively, per mole of the compound of the formula (III).

The reaction for yielding the hydrazoic acid salt of compound of the formula (III) is carried out at any temperature from 0° C. to the reflux temperature of the reaction solvent used, and usually at about room temperature.

As the reaction solvent, there can be used those used in the Process (A).

The thus obtained hydrazoic acid salt of compound of the formula (III) is reacted with a compound of the formula (VI) without separation from the reaction solution to yield the compound of the formula (V).

The compound of the formula (VI) is usually used in an amount of 1 mole or more, preferably 1 to about 2 moles, per mole of the compound of the formula (III).

The compound of the formula (VI) can be added to the reaction solution either after the formation of the hydrazoic acid salt of compound of the formula (III) or from the initial time.

The reaction between the hydrazoic acid salt of compound of the formula (III) and the compound of the formula (VI) is carried out usually at 0° C. to the reflux temperature of the reaction solvent used. A higher reaction temperature is preferable from the viewpoint of shortening the reaction time.

The identification of formation of the compound of the formula (V), the ring closure reaction of the compound of the formula (V) and aftertreatment of the resulting compound of the formula (I) can be carried out in the same manner as described in the Process (A).

(3) Process (C)

In this process, a compound of the formula (VII) and an alkyl orthoformate are used in place of the compound of the formula (VI) in the Process (B).

As the alkyl orthoformate, there can be used, for example, methyl orthoformate, ethyl orthoformate, and the like, described in the Process (A).

The compound of the formula (VII) and the alkyl orthoformate can be used in amounts of usually 1 mole or more, preferably 1 mole to about 2 moles, respectively, per mole of the compound of the formula (III).

Other reaction conditions such as the reaction solvent, the reaction temperature, etc., and the aftertreatment are the same as described in the Process (B).

As mentioned above, the Processes (B) and (C) include the tetrazole cyclization reaction in a series of reaction procedure unlike the Process (A).

According to a known tetrazole cyclization reaction, ammonium chloride, aluminum chloride, or the like is usually added to the reaction system containing sodium azide or the like in order to enhance the reactivity by changing the sodium azide to ammonium azide or aluminum azide. But even if ammonium chloride or aluminum chloride are added to the reaction system, the yield is about 50% at most. Such a yield is not so high. Further, there arise various troubles by using ammonium chloride or aluminum chloride. For example, in the case of using ammonium chloride, sodium azide acts as ammonium azide which is very high in sublimation, and released out of the reaction system when reacted at high temperatures for a long period of time, resulting in requiring a large excess amount of ammonium chloride. This is undesirable from the viewpoint of efficiency. On the other hand, in the case of using aluminum chloride, sodium azide acts in the reaction system as a polyvalent metal salt of hydrazoic acid such as aluminum azide which is a very dangerous compound due to its explosiveness. Thus, a much care and skill are necessary for handling such a compound. Further, when such a polyvalent metal salt is used in the reaction, since a large amount of azide group not pertaining to the tetrazole cyclization reaction is retained after the reaction, there is produced a large amount of hydrogen azide, resulting in causing a problem of air pollution. Thus, waste disposal of metal due to aluminum is also required.

Therefore, according to the known method, in order to apply such a reaction to practical production, there are required improvement of the yield, solving of problems of working circumstances, safety of workers, air pollution, industrial waste disposal, and the like.

In contrast, according to the present invention, since the compound of the formula (III) which is used as a starting material and also has a catalytic action, the use of ammonium chloride or aluminum chloride is not necessary. Thus, even if the tetrazole cyclization is conducted, since no ammonium chloride or aluminum chloride are used, no problems as mentioned above take place. In addition, since the kinds and amounts of additives to be added to the reaction system are none or a little (e.g. no catalyst is used), insertion of contaminants into the reaction product is non or a little. This is very favorable for synthesizing medicines.

In the Processes (A) to (C), when the compounds of the formulae (III) to (VII) have functional groups in the substituents $R^1$ to $R^9$ to be protected during the reaction, steps of introducing a protective group and removing the protective group can be inserted into the reaction.

Further, when the compounds of the formulae (III) to (VII) have tautomers, any of them can be used in the reaction.

The present invention is illustrated by way of the following Examples.

EXAMPLE 1

In 20 ml of dimethylformamide, 5.4 g (50 mmoles) of 2-amino-3-methylpyridine, 7.8 g (50 mmoles) of ethyl 1

H-tetrazol-5-yl-acetate and 8.2 g (55 mmoles) of ethyl orthoformate were dissolved and reacted at 90° C. for 1 hour with stirring. After the reaction, 55 ml of 1N potassium hydroxide was added to the reaction solution and stirring was continued at 50° C. for 1 hour. After cooling, the reaction solution was acidified with 10% HCl to deposit crystals, followed by filtration. As a result, 9.4 g of white needles of 9-methyl-3-1 H-tetrazol-5-yl-4 H-pyrido[1,2-a]pyrimidin-4-one was obtained in yield of 82%.

EXAMPLE 2

In 20 ml of tetrahydrofuran, 5.4 g (50 mmoles) of 2-amino-3-methylpyridine, 7.8 g (50 mmoles) of ethyl 1 H-tetrazol-5-yl-acetate and 8.2 g (55 mmoles) of ethyl orthoformate were dissolved and refluxed for 6 hours with stirring. After cooling, 13.3 g (100 mmoles) of anhydrous aluminum chloride was added to the reaction solution and refluxed for 6 hours with stirring. After cooling, water was added to the reaction solution, followed by filtration. As a result, 3.7 g of white needles of 9-methyl-3-1 H-tetrazol-5-yl-4 H-pyrido[1,2-a]-pyrimidin-4-one was obtained in yield of 32%.

EXAMPLE 3

The process of Example 1 was repeated except for using 2-amino-3-(4-acetyl-3-hydroxy-2-n-propyl-phenoxymethyl)pyridine in place of 2-amino-3-methyl-pyridine to give 19.7 g of white crystals of 9-(4-acetyl-3-hydroxy-2-n-propylphenoxymethyl)-3-1 H-tetrazol-5-yl-4 H-pyrido[1,2-a]pyrimidin-4-one in yield of 94%.

EXAMPLE 4

In 20 ml of dimethylformamide, 7.3 g (50 mmoles) of 2-amino-3-methylpyridine hydrochloride and 3.8 g (50 mmoles) of sodium azide were suspended and stirred at room temperature for 1 hour, followed by addition of 8.5 g (50 mmoles) of ethyl ethoxymethylenecyanoacetate and stirring at 90° C. for 6 hours with heating. After the reaction, 55 ml of 1N KOH was added to the reaction solution. Stirring was continued at 50° C. for 1 hour. After cooling, the reaction solution was acidified with 10% HCl to deposit crystals. After filtration, 7.0 g of white needles of 9-methyl-3-1 H-treazol-5-yl-4 H-pyrido[1,2-a]pyrimidin-4-one was obtained in yield of 62%.

EXAMPLE 5

In 20 ml of dimethylformamide, 7.3 g (50 mmoles) of 2-amino-3-methylpyridine hydrochloride and 3.8 g (50 mmoles) of sodium azide were suspended and stirred at room temperature for 1 hour, followed by addition of 8.5 g (50 mmoles) of ethyl ethoxymethylene cyanoacetate and stirring at 90° C. for 6 hours with heating. After cooling, 10 ml of phosphorus oxychloride was added to the reaction solution and stirring was continued at 90° C. for 5 hours. After cooling, water was added to the reaction solution, followed by filtration. As a result, 2.9 g of white needles of 9-methy-3-1 H-tetrazol-5-yl-4 H-pyrido[1,2-a]pyrimidin-4-one was obtained in yield of 26%.

EXAMPLE 6

In 20 ml of dimethylformamide, 7.3 g (50 mmoles) of 2-amino-3-methylpyridine hydrochloride and 3.8 g (50 mmoles) of sodium azide were suspended and stirred at room temperature for 1 hour, followed by addition of 6.1 g (50 mmoles) of ethyl cyanoacetate and 11.2 g (75 mmoles) of ethyl orthoformate thereto. Stirring was conducted at 90° C. for 12 hours. After the reaction, 55 ml of 1N KOH was added to the reaction solution. Stirring was continued at 50° C. for 1 hour. After cooling, the reaction solution was acidified with 10% HCl to deposit crystals. After filtration, 6.5 g of white needles of 9-methyl-3-1 H-tetrazol-5-yl-4 H-pyrido[1,2-a]pyrimidin-4-one was obtained in yield of 57%.

EXAMPLE 7

In 20 ml of dimethylformamide, 5.4 g (50 mmoles) of 2-amino-3-methylpyridine and 3.8 g (50 mmoles) of sodium azide were suspended, followed by addition of 4.9 g (50 mmoles) of sulfuric acid and stirring at room temperature for 1 hour. To this, 8.5 g (50 mmoles) of ethyl ethoxymethylenecyanoacetate was added. After stirring at 90° C. for 6 hours with heating, 55 ml of 1N KOH was added to the reaction solution, followed by stirring at 50° C. for 1 hour. After cooling, the reaction solution was acidified with 10% HCl to deposit crystals. After filtration, white needles of 6.0 g of 9-methyl-3-1 H-tetrazol-5-yl-4 H-pyrido[1,2-a]pyrimidin-4-one were obtained in yield of 53%.

EXAMPLE 8

In 20 ml of dimethylformamide, 7.3 g (50 mmoles) of 2-amino-3-methylpyridine hydrochloride and 3.8 g (50 mmoles) of sodium azide were suspended, followed by stirring at room temperature for 1 hour. Then, 6.1 g (50 mmoles) of ethoxymethylenemalononitrile was added to the reaction solution, followed by stirring at 90° C. for 6 hours with heating. After the reaction, 150 ml of concentrated HCl was added to the reaction solution, followed by heating at 110° C. for 4 hours with stirring. After cooling, deposited crystals were filtered to give 6.7 g of white needles of 9-methyl-3-1 H-tetrazol-5-yl-4 H-pyrido[1,2-a]pyrimidin-4-one in yield of 59%.

EXAMPLE 9

In 20 ml of dimethylformamide, 7.3 g (50 mmoles) of 2-amino-3-methylpyridine hydrochloride and 3.8 g (50 mmoles) of sodium azide were suspended. After stirring at room temperature for 1 hour, 3.3 g (50 mmoles) of malononitrile and 11.2 g (75 mmoles) of ethyl orthoformate were added to the reaction solution, followed by stirring at 90° C. for 12 hours with heating. After the reaction, 150 ml of concentrated HCl was added to the reaction solution, followed by heating at 110° C. for 4 hours with stirring. After cooling, deposited crystals were filtered to give 5.8 g of white needles of 9-methyl-3-1 H-tetrazol-5-yl-4 H-pyrido[1,2-a]-pyrimidin-4-one in yield of 51%.

As mentioned above, pyrido[1,2-a]pyrimidine derivatives having a complicated structure can be obtained from a commercially available simple compound by one-pot reaction in high yield. Thus, various pyrido[1,2-a]pyrimidine derivatives useful as antiallergic agent can be produced with extremely low cost in a short time.

What is claimed is:

1. A process for producing a compound of the formula (I):

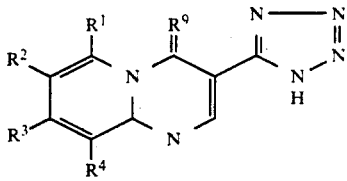 (I)

wherein $R^1$ and $R^3$ are independently a hydrogen atom or a lower alkyl group having 1 to 6 carbon atoms; $R^2$ and $R^4$ are independently a hydrogen atom, a halogen atom, a lower alkyl group having 1 to 6 carbon atoms, a lower alkoxy group having 1 to 6 carbon atoms, a phenyl group or a group of the formula (II):

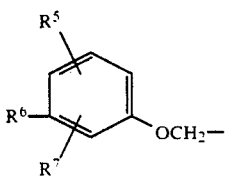 (II)

wherein $R^5$ is a hydrogen atom or a hydroxyl group; $R^6$ is a hydrogen atom, or an acetyl group, a propionyl group, a butyryl group or a benzoyl group; $R^7$ is a hydrogen atom, a lower alkyl group having 1 to 6 carbon atoms or an allyl group; and $R^9$ is an oxygen atom, which comprises reacting a compound of the formula (III):

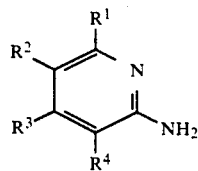 (III)

wherein $R^1$ to $R^4$ are as defined above, with a compound of the formula (IV):

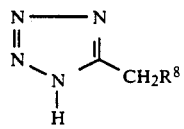 (IV)

wherein $R^8$ is a lower alkoxycarbonyl group having 2 to 7 carbon atoms, and a $C_{1-6}$ alkyl orthoformate, in the absence of a catalyst, to yield a compound of the formula (V):

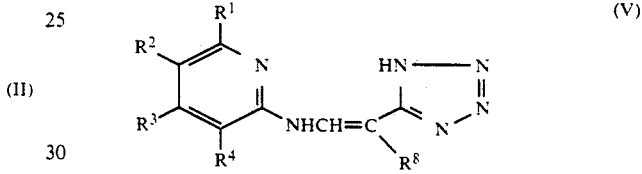 (V)

wherein $R^1$ to $R^4$ and $R^8$ are as defined above, and subjecting the compound of the formula (V) to a ring closure reaction in the presence of a base selected from the group consisting of a caustic alkali, a hydroxide of alkaline earth metal, a metal alkoxide, an organic base and ammonia, wherein the base for the ring closure reaction is added in an amount sufficient for forming a physiologically acceptable salt of a compound of the formula (I), followed by isolation of the reaction product without neutralization.

2. A process according to claim 1, wherein the reaction for producing the compound (V) is carried out in an organic solvent selected from the group consisting of alcohols, ketones, esters, aromatic hydrocarbons, halogenated hydrocarbons, nitriles, ethers, amides and sulfoxides.

* * * * *